US010820794B2

(12) United States Patent
Utsunomiya et al.

(10) Patent No.: US 10,820,794 B2
(45) Date of Patent: Nov. 3, 2020

(54) PUPIL MONITORING METHOD FOR ADAPTIVE OPTICS IMAGING SYSTEM

(71) Applicant: CANON KABUSHIKI KAISHA, Tokyo (JP)

(72) Inventors: Norihiko Utsunomiya, Port Washington, NY (US); Koji Nozato, Rochester, NY (US)

(73) Assignee: CANON KABUSHIKI KAISHA, Tokyo (JP)

( * ) Notice: Subject to any disclaimer, the term of this patent is extended or adjusted under 35 U.S.C. 154(b) by 244 days.

(21) Appl. No.: 14/935,235

(22) Filed: Nov. 6, 2015

(65) Prior Publication Data
US 2017/0127931 A1 May 11, 2017

(51) Int. Cl.
*A61B 3/11* (2006.01)
*A61B 3/12* (2006.01)
*G02B 27/00* (2006.01)
*A61B 3/10* (2006.01)
*G02B 26/06* (2006.01)

(52) U.S. Cl.
CPC ............ *A61B 3/111* (2013.01); *A61B 3/102* (2013.01); *A61B 3/1025* (2013.01); *A61B 3/12* (2013.01); *G02B 26/06* (2013.01); *G02B 27/0068* (2013.01)

(58) Field of Classification Search
None
See application file for complete search history.

(56) References Cited

U.S. PATENT DOCUMENTS

| 6,964,480 B2 | 11/2005 | Levine |
| 7,237,898 B1 | 7/2007 | Hohla et al. |
| 7,338,164 B2 | 3/2008 | Persoff |

(Continued)

FOREIGN PATENT DOCUMENTS

CN 101862178 A 10/2010

OTHER PUBLICATIONS

Norberto López-Gil, José Francisco Castejón-Mochón, Vicente Fernández-Sánchez, Limitations of the Ocular Wavefront Correction with Contact Lenses, Vision Research, Apr. 21, 2009, vol. 49, No. 14, pp. 1729-1737, Elsevier Ltd., Amsterdam, NL, 2009.

(Continued)

*Primary Examiner* — Darryl J Collins
*Assistant Examiner* — Journey F Sumlar
(74) *Attorney, Agent, or Firm* — Canon U.S.A., Inc. IP Division

(57) ABSTRACT

An ophthalmic image processing method, a non-transitory computer readable medium encoded with instructions for a computer to perform a method for processing images from an ophthalmic apparatus and an ophthalmic apparatus that irradiates an eye of a subject and gathers return light from a fundus of the eye. The ophthalmic apparatus may also comprise a wavefront sensor. The wavefront sensor may output to the memory, wavefront information that is representative of a wavefront of the return light from the fundus. The ophthalmic apparatus may also comprise a pupil monitor. The pupil monitor may output to the memory, a macro ocular portrait of the eye. The processor may produce an overlay image in which the wavefront information is overlaid on top of the macro ocular portrait.

19 Claims, 11 Drawing Sheets

(56) References Cited

U.S. PATENT DOCUMENTS

| | | | |
|---|---|---|---|
| 7,416,305 | B2 | 8/2008 | Williams et al. |
| 7,466,413 | B2 | 12/2008 | Finders et al. |
| 7,784,941 | B2 | 8/2010 | Fukuma et al. |
| 7,988,293 | B2 | 8/2011 | Raymond et al. |
| 8,596,790 | B2 | 12/2013 | Salvati et al. |
| 8,882,270 | B2 | 11/2014 | Zhou et al. |
| 2011/0230751 | A1* | 9/2011 | Kersting ............ A61F 9/00736 600/407 |
| 2013/0308098 | A1 | 11/2013 | Levecq et al. |
| 2014/0055748 | A1 | 2/2014 | Saito |
| 2014/0125949 | A1 | 5/2014 | Shea et al. |
| 2015/0150450 | A1* | 6/2015 | Nozato ................ A61B 3/1025 351/206 |
| 2016/0249803 | A1* | 9/2016 | Saito ........................ A61B 3/12 351/221 |

OTHER PUBLICATIONS

J. C. He, S. Marcos, R. H. Webb, S. A. Burns, Measurement of the Wave-Front Aberration of the Eye by a Fast Psychophysical Procedure, Journal of the Optical Society of America A, vol. 15, No. 9, Sep. 1, 1998, pp. 2449-2456, OSA, Washington DC, 1998.

Frantz Martinache, The Asymmetric Pupil Fourier Wavefront Sensor, Mar. 26, 2013, Preprint.

Yan Zhang, Barry Cense, Jungtae Rha, Ravi S. Jonnal, Weihua Gao, Robert J. Zawadzki, John S. Werner, Steve Jones, Scot Olivier, Donald T. Miller, High-Speed Volumetric Imaging of Cone Photoreceptors with Adaptive Optics Spectral-Domain Optical Coherence Tomography, Optics Express, May 15, 2006, vol. 14, No. 10, pp. 4380-4394, OSA, Washington DC, 2006.

* cited by examiner

200

PUPIL MONITORING METHOD FOR ADAPTIVE OPTICS IMAGING SYSTEM

BACKGROUND

Field of Art

The present disclosure relates to a system and method for controlling an ophthalmoscope.

Description of the Related Art

Ophthalmoscope and ophthalmic image pickup apparatuses such as: scanning laser ophthalmoscopes (SLOs) that irradiate the fundus with a laser in two dimensions; and optical coherence tomographs (OCTs) that utilizes the interference of low coherence light have been developed and commercialized. Thus, SLOs and OCTs have become important tools for the study of the human retina in both normal and diseased eyes.

The resolution of such SLOs have been improved by, for example, achieving high NA of irradiation laser light. However, when an image of the fundus is to be acquired, the image must be acquired through optical tissues including the cornea and the crystalline lens. As the resolution increases, the aberrations of the cornea and the crystalline lens have come to significantly affect the quality of the acquired images.

The use of adaptive optics (AO) in AO-SLO and AO-OCT in which the AO is an optical correction system that both measures the aberration of the eye and corrects the aberration of the eye have been incorporated into optical measurement systems. The AO-SLO and/or AO-OCT generally measure the wavefront of the eye using a Shack-Hartmann wavefront sensor system. A deformable mirror or one or more spatial-phase modulator(s) are driven to correct the measured wavefront. After which an image of the fundus is acquired, thus allowing the AO-SLO and/or AO-OCT to acquire high-resolution images.

Control of the AO system is done via a feedback loop system. The step of measuring aberrations and correcting the measured aberrations are processed one after another continuously. In an AO system, measurement of pupil aberration is important so as to compensate for the aberration. To measure the aberration precisely, it is important to keep the pupil position at an appropriate location in the horizontal, the vertical relative to the light axis. The ophthalmoscope includes a pupil exterior monitoring camera which produce an macro ocular video portrait so as to monitor a subject's pupil position and condition. The AO-SLO and the AO-OCT also have pupil monitors. The pupil monitor can be used for monitoring pupil position along the light axis direction by measuring the focusing status or one or more other indicators.

It is also important to check the Shack-Hartmann image produced by the Shack-Hartmann sensor to make sure that sufficient spots are detected and inappropriate light doesn't come into the sensor for accurate wavefront measuring. Spots may disappear because of eye lid, eyelash, cataract, or some other reason. These factors which can cause measurement failures should be resolved before imaging of the fundus is performed.

It can be difficult to monitor both images because these two images are displayed separately and they are not linked. Operators of the ophthalmoscope can have difficulty seeing the relationship between these two images. For example, even if some Shack-Hartmann spots do disappear, the operator can have difficulty identifying the cause of the disappearance. Many factors can affect the Shack-Hartmann image such as pupil size, eye lid, eye lash, cataract, etc. It can be difficult for an operator to identify the source of the problems so that the operator can attempt to solve the problem and thus produce a quality Shack-Hartmann image.

What is needed are systems and methods for providing information to an operator that helps the operator obtain high quality images.

SUMMARY

One embodiment may be an ophthalmic apparatus that irradiates an eye of a subject and gathers return light from a fundus of the eye. The ophthalmic apparatus may comprise a processor and a memory. The ophthalmic apparatus may also comprise a wavefront sensor. The wavefront sensor may output to the memory, wavefront information that is representative of a wavefront of the return light from the fundus. The ophthalmic apparatus may also comprise a pupil monitor. The pupil monitor may output to the memory, a macro ocular portrait of the eye. The processor may produce an overlay image in which the wavefront information is overlaid on top of the macro ocular portrait.

In another embodiment, the wavefront sensor may be a Shack-Hartmann sensor. The wavefront information may be represented in the overlay image as a Shack-Hartmann image.

In another embodiment, the wavefront information may be represented in the overlay image in a different color from the color used in the macro ocular portrait in the overlay image.

In another embodiment, the overlay image may further comprise a first target. Wherein, the first target may be overlaid over the macro ocular portrait. The first target may represent an area of the eye that is irradiated by the ophthalmic apparatus. The first target position and a first target diameter of the first target may be set during a calibration process. A relative position of the first target position may move relative to the macro ocular portrait if the position of the area of the eye that is irradiated by the ophthalmic apparatus moves. The first target diameter may change relative to the macro ocular portrait if the area of the eye that is irradiated by the ophthalmic apparatus changes in size. A first target color of the first target may change based on one or more of: a number of detected spots in the wavefront information; an average signal strength of the detected spots in the wavefront information; and a presence of artifacts in the wavefront information.

In another embodiment, the overlay image may further comprise: a second target which may be overlaid over the macro ocular portrait, wherein the second target is representative of an area of a pupil that is calculated on the basis of the wavefront information. A second target color of the second target may change based upon one or more of: a diameter of the detected area of the pupil; and presence of artifacts in the macro ocular portrait.

In another embodiment, the overlay image may further comprise aberration information of the eye that is calculated on the basis of the wavefront information.

In another embodiment, the overlay image may be displayed on a display unit in response to receiving a display mode setting to display the overlay image.

In another embodiment, the ophthalmic apparatus may further comprise a display unit to display the overlay image.

In another embodiment, the processor may produce a time series of overlay images as an overlay video. A wavefront refresh rate of the wavefront information may be different from a macro ocular portrait refresh rate of the macro ocular portrait. An overlay video refresh rate may be the greater of the wavefront refresh rate and the macro ocular portrait refresh rate.

In another embodiment, the processor may remove artifacts from the overlay image, wherein the artifacts come from the macro ocular portrait.

In another embodiment, the wavefront information may be represented by a plurality of markers. Each marker among the plurality of markers may represent detected wavefront information in a particular area of the fundus. Each marker among the plurality of markers may be displayed with a particular marker color. The particular marker color may be selected from a range of marker colors. The particular marker color for each particular marker may be selected based upon one or more of: a signal strength of the detected wavefront information in the particular area of the fundus; a magnitude of local aberration associated with the detected wavefront information in the particular area of the fundus; and a direction of local aberration associated with the detected wavefront information in the particular area of the fundus.

In another embodiment, each marker may be a spot, a diameter of each spot is correlated with the magnitude of the local aberration. In another embodiment, each marker may be a vector. A length of each vector may be correlated with the magnitude of the local aberration. The direction of each vector may be correlated with the direction of the local aberration.

Another embodiment, is an ophthalmic image processing method for images from an ophthalmic apparatus. The ophthalmic image processing method may include receiving wavefront information that is representative of a wavefront of return light from a fundus of an eye. The ophthalmic image processing method may include receiving a macro ocular portrait of the eye. The ophthalmic image processing method may include producing an overlay image in which the wavefront information is overlaid on top of the macro ocular portrait.

Another embodiment is a non-transitory computer readable medium encoded with instructions for a computer to perform a method for processing images from an ophthalmic apparatus. The instructions for the computer may include receiving wavefront information that is representative of a wavefront of return light from a fundus of an eye. The instructions for the computer may include receiving a macro ocular portrait of the eye. The instructions for the computer may include producing an overlay image in which the wavefront information is overlaid on top of the macro ocular portrait.

BRIEF DESCRIPTION OF THE DRAWINGS

The accompanying drawings, which are incorporated in and constitute a part of the specification, illustrate exemplary embodiments.

DESCRIPTION OF THE EMBODIMENTS

Figure 1:
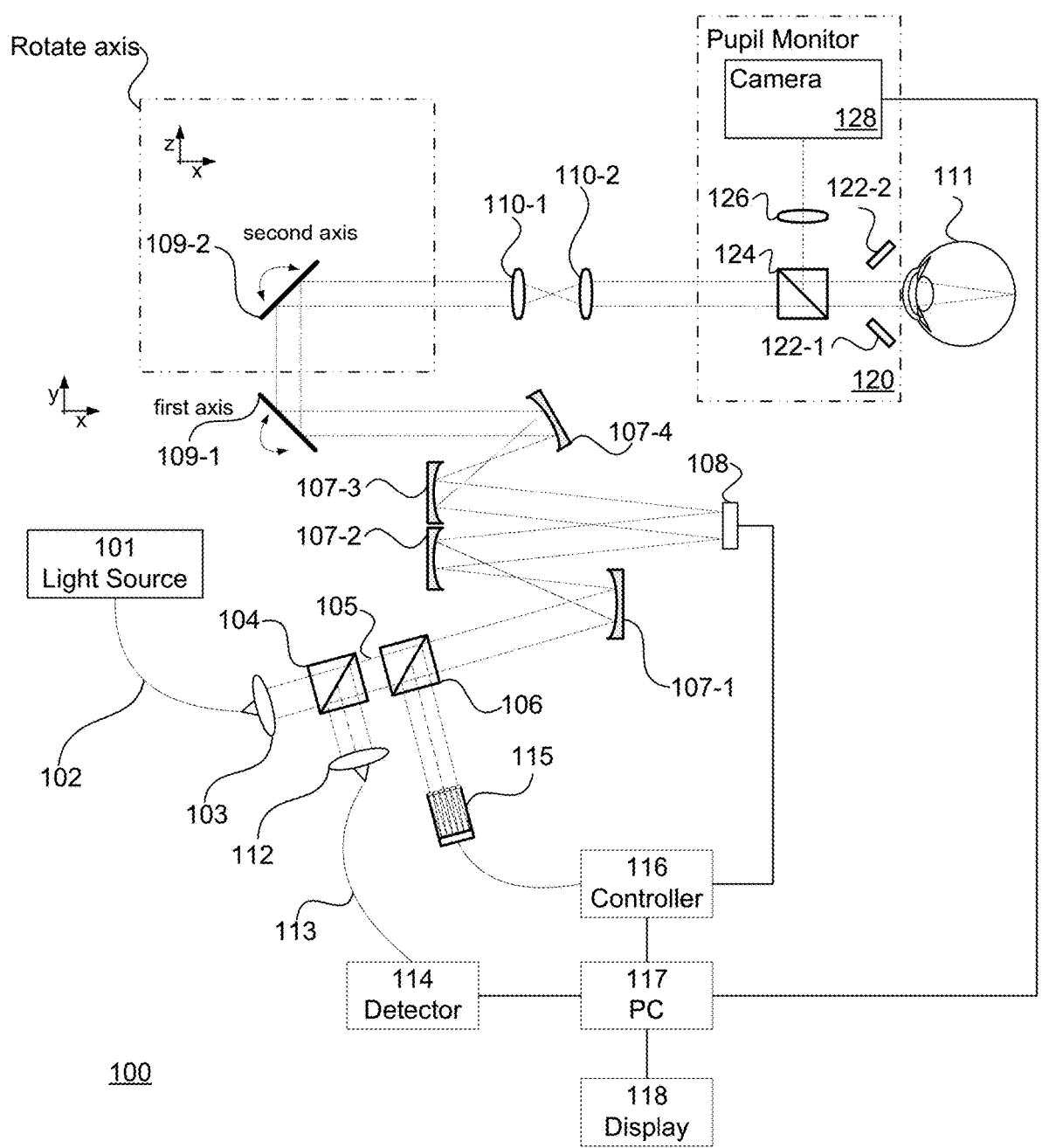
FIG. 1 is an illustration of an ophthalmoscope in which an embodiment may be implemented.

Embodiments will be described below with reference to the attached drawings. Like numbers refer to like elements throughout. Exemplary embodiments will be described in detail with reference to the drawings below. It shall be noted that the following description is merely illustrative and exemplary in nature, and is in no way intended to limit the disclosure and its applications or uses. The relative arrangement of components and steps, numerical expressions and numerical values set forth in the embodiments do not limit the scope of the disclosure unless it is otherwise specifically stated. Techniques, methods, and devices which are well known by individuals skilled in the art may not have been discussed in detail since an individual skilled in the art would not need to know these details to enable the embodiments discussed below. Further, an image photographing apparatus as disclosed in the following which is used inspect an eye as described below may also be used to inspect other objects including but not limited to skin, and internal organs.

Ophthalmoscope

A first embodiment is described with reference to of a fundus image photographing apparatus (ophthalmoscope) such as the photographing apparatus illustrated in FIG. 1.

Embodiments are directed towards systems, methods, non-transitory computer readable medium, and software which are used in connection with an imaging system such as an ophthalmoscope 100. FIG. 1 is an illustration of an exemplary ophthalmoscope 100. An ophthalmoscope 100 is a system or apparatus for obtaining information about an interior portion of the eye 111 (e.g., the fundus).

An exemplary embodiment may be a scanning ophthalmoscope. A scanning ophthalmoscope scans a spot across the eye 111. The spot may be a spot of light from a light source 101 that is scanned across the eye 111.

In an exemplary embodiment 100, the spot of light is produced by a light source 101. The light source 101 may be incorporated into the ophthalmoscope 100; alternatively, the ophthalmoscope 100 may include an input for receiving the light source 101. The input for the light source 101 may be a fiber optic input or a free space input. The light source 101 may be a laser, a broadband light source, or multiple light sources. In an exemplary embodiment, the light source 101 is a super luminescent diode (SLD) light source having a wavelength of 840 nm. The wavelength of the light source 101 is not particularly limited, but the wavelength of the light source 101 for fundus image photographing is suitably set in a range of approximately 800 nm to 1,500 nm in order to reduce glare perceived by a person being inspected and to maintain imaging resolution.

In an exemplary embodiment, light emitted from the light source 101 passes through a single-mode optical fiber 102, and is radiated as collimated light (measuring light 105) by a collimator 103.

In exemplary an embodiment, the polarization of the irradiated light may be adjusted by a polarization adjusting member 119 (not shown) provided in a path of the single-mode optical fiber 102. In an alternative configuration, the light source 101 is polarized and single-mode optical fiber 102 is polarization maintain fiber. In another configuration, the polarization adjusting member may be placed after the collimator 103. Alternatively, the polarization adjusting member may be replaced with a polarizer.

The measuring light 105 radiated from the collimator 103 passes through a light division portion 104 including a beam splitter. An exemplary embodiment includes an adaptive optical system.

The adaptive optical system may include a light division portion 106, a wavefront sensor 115, wavefront adjustment device 108, and reflective mirrors 107-1 to 107-4 for guiding the measuring light 105 to and from those components. The reflective mirrors 107-1 to 107-4 are provided to guide the measuring light 105 to and from the pupil of an eye 111, the wavefront sensor 115, and the wavefront adjustment device 108. The reflective mirrors may be replaced with suitable optics, such as lenses and/or apertures. The wavefront sensor 115 and the wavefront adjustment device 108 may be in an optically conjugate relationship. A beam splitter may be used as the light division portion 106. The wavefront sensor 115 may be a Shack-Hartmann sensor or other type of sensor that gathers information that is representative of the wavefront of light coming from the subject.

The measuring light 105 passing through the light division portion 106 is reflected by the reflective mirrors 107-1 and 107-2 so as to enter the wavefront adjustment device 108. The measuring light 105 is reflected by the wavefront adjustment device 108 and is further reflected by the reflective mirrors 107-3 and 107-4.

The wavefront adjustment device 108 maybe a transmissive device or a reflective device. The wavefront adjustment device 108, is an addressable spatial light phase modulator that allows relative phases across a beam coming into the wavefront adjustment device 108 to be adjusted such that relative phases across the beam coming out of the wavefront adjustment device 108 are adjustable. In an exemplary embodiment, one or two spatial phase modulators including a liquid crystal element is used as the wavefront adjustment device 108. The liquid crystal element may modulate a phase of only a specific polarized component. In which case, two liquid crystal elements may be employed to modulate substantially orthogonal polarized components of the measuring light 105. In an alternative embodiment, the wavefront adjustment device 108 is a deformable mirror.

The measuring light 105 reflected off mirror 107-4 is two-dimensionally scanned by a scanning optical system 109. In an exemplary embodiment, the scanning optical system 109 includes a first scanner 109-1 and a second scanner 109-2. The first scanner 109-1 rotates around the first axis, while the second scanner 109-2 rotates around a second axis. The first axis is substantially orthogonal to the second axis. Substantially in the context of the present disclosure means within the alignment and measurement tolerances of the system.

FIG. 1 illustrates the first scanner 109-1 rotating in the x-y plane, while the second scanner 109-2 is rotating in the z-x plane. In the context of the present disclosure, rotating the measuring light 105 in a first plane around the first axis is equivalent to rotating the measuring light 105 in the first plane and is equivalent to scanning the spot of light in the main scanning direction or the lateral direction of the object being imaged. In the context of the present disclosure, rotating the measuring light 105 in a second plane around the second axis is equivalent to rotating the measuring light 105 in the second plane and is equivalent to scanning the spot of light in the sub-scanning direction or the longitudinal direction of the object being imaged. The sub-scanning direction is substantially orthogonal to the main scanning direction.

A scanning period of the first scanner 109-1 is less than the scanning period of the second scanner 109-2. The order of the first scanner 109-1 and the second scanner 109-2 may be exchanged without impacting the operation of an exemplary embodiment. The first scanner 109-1 may operate in a resonant scanning mode.

In an exemplary embodiment, the scanning optical system 109 may be a single tip-tilt mirror that is rotated around the first axis and around the second axis that is substantially orthogonal to the first axis. An exemplary embodiment may also use non-mechanical beam steering techniques.

In an exemplary embodiment, the first scanner 109-1 and the second scanner 109-2 are galvano-scanners. In another exemplary embodiment, one of the first scanner 109-1 and the second scanner 109-2 is a resonant scanner. The resonant scanner may be used for the main scanning direction. The resonant scanner may be tuned to oscillate at a specific frequency. There may be additional optical components, such as lenses, mirrors, apertures, and etc. between the scanners 109-1, 109-2, and other optical components. These additional optical components may be arranged such that the light is focused onto the scanners, in a manner that is optically conjugate with all of or one or more of the subject 111, the wavefront adjustment device 108, the wavefront sensor 115, and a detector 114.

The measuring light 105 scanned by the scanning optical system 109 is radiated to the eye 111 through eyepieces 110-1 and 110-2. The measuring light radiated to the eye 111 is reflected, scattered, or absorbed on the fundus. When the eyepieces 110-1 and 110-2 are adjusted in position, suitable irradiation may be performed in accordance with the diopter of the eye 111. Lenses may be used for the eyepiece portion in this embodiment, but other optical components such as spherical mirrors may also be used.

Light which is produced by reflection, fluorescence, or scattering on a retina of the eye 111 then travels in the reverse direction along the same path as in the case of incident light. A part of the reflected light is reflected by the light division portion 106 to the wavefront sensor 115 to be used for measuring a light beam wavefront.

In an exemplary embodiment, a Shack-Hartmann sensor is used as the wavefront sensor 115. However, an exemplary embodiment is not limited to a Shack-Hartmann sensor. Another wavefront measurement unit, for example, a curvature sensor may be employed or a method of obtaining the wavefront by reverse calculation from the formed spot images may also be employed.

In FIG. 1, when the reflected light passes through the light division portion 106, a part thereof is reflected on the light division portion 104 and is guided to a light intensity sensor 114 through a collimator 112 and an optical fiber 113. The light intensity sensor 114 converts the light into an electrical signal. The electrical signal is processed by a control unit 117 into an image of the object, and the image is displayed on a display 118.

The wavefront sensor 115 is connected to an adaptive optics control unit 116. The received wavefront is transferred to the adaptive optics control unit 116. The wavefront adjustment device 108 is also connected to the adaptive optics control unit 116 and performs modulation as instructed by the adaptive optics control unit 116. The adaptive optics control unit 116 calculates a modulation amount (correction amount) for correction to obtain a wavefront having no aberration based on the wavefront obtained by a measuring result of the wavefront sensor 115, and instructs the wavefront adjustment device 108 to perform the modulation according to the modulation amount. The wavefront measurement and the instruction to the wavefront adjustment device are repeated and feedback control is performed so as to obtain a suitable wavefront.

In an exemplary embodiment the light division portions 104 and/or 106 are fused fiber couplers. In an alternative exemplary embodiment, the light division portions 104 and/or 106 may include partially reflective mirrors. In another alternative exemplary embodiment, the light division portions 104 and/or 106 may include dichroic reflectors, in which case a different wavelength of light is used for detecting the phase than is used for detecting the spatial phase image.

The detector 114 may detect reflections or fluorescence associated with the scanning spot. The detection system may make use confocal microscopy techniques in which an aperture associated with the scanning spot is used to increase the resolution and/or contrast of the detection system.

The adaptive optics system described above includes at least the wavefront sensor 115 and the wavefront adjustment device 108 so that the aberration of the subject's eyes can be measured and compensated for. A deformable mirror (DM) or a spatial light phase modulator (SLM) can be used as the wavefront adjustment device 108. Since the typical SLM has a large number of actuators, it can modulate wavefront more precisely than DM can. A liquid crystal on silicon spatial light modulator (LCOS-SLM) may be used as the wavefront adjustment device 108. The LCOS-SLM 108 can be controlled to provide a precise spatial modulation of the phase of the beam that is used to illuminate the subject.

The optical system 100 also includes pupil monitor 120. The pupil monitor 120 includes a light source 122. The light source 122 may include two light sources 122-1 and 122-2 that are symmetrically arranged around the optical axis so as to provide a balanced illumination of the pupil. The light source 122 may be a visible light source or some other wavelength. The wavelength of the light source 122 may be different from the light source 101 used to measure the fundus. The pupil monitor 120 may also include beam splitter 124. The beam splitter 124 may be a dichroic filter. The pupil monitor 120 may also include a lens 126. The pupil monitor 120 includes a camera 128. The camera 128 may be a CCD. In alternative embodiment, the wavelength of the light source 122 may have the same wavelength as the light source 101, in which case the beam splitter 124 is not a dichroic filter and the light sources 122 and 101 may be modulated.

Images Obtained with Ophthalmoscope

The ophthalmoscope 100 uses an adaptive optics measurement of the pupil aberration with the wavefront sensor 115 so as to compensate for the aberrations with the wavefront adjustment device 108. To measure the aberration precisely, it is important to keep the pupil position at an appropriate location in along the horizontal axis, the vertical axis, and along the light axis direction.

Figure 2:
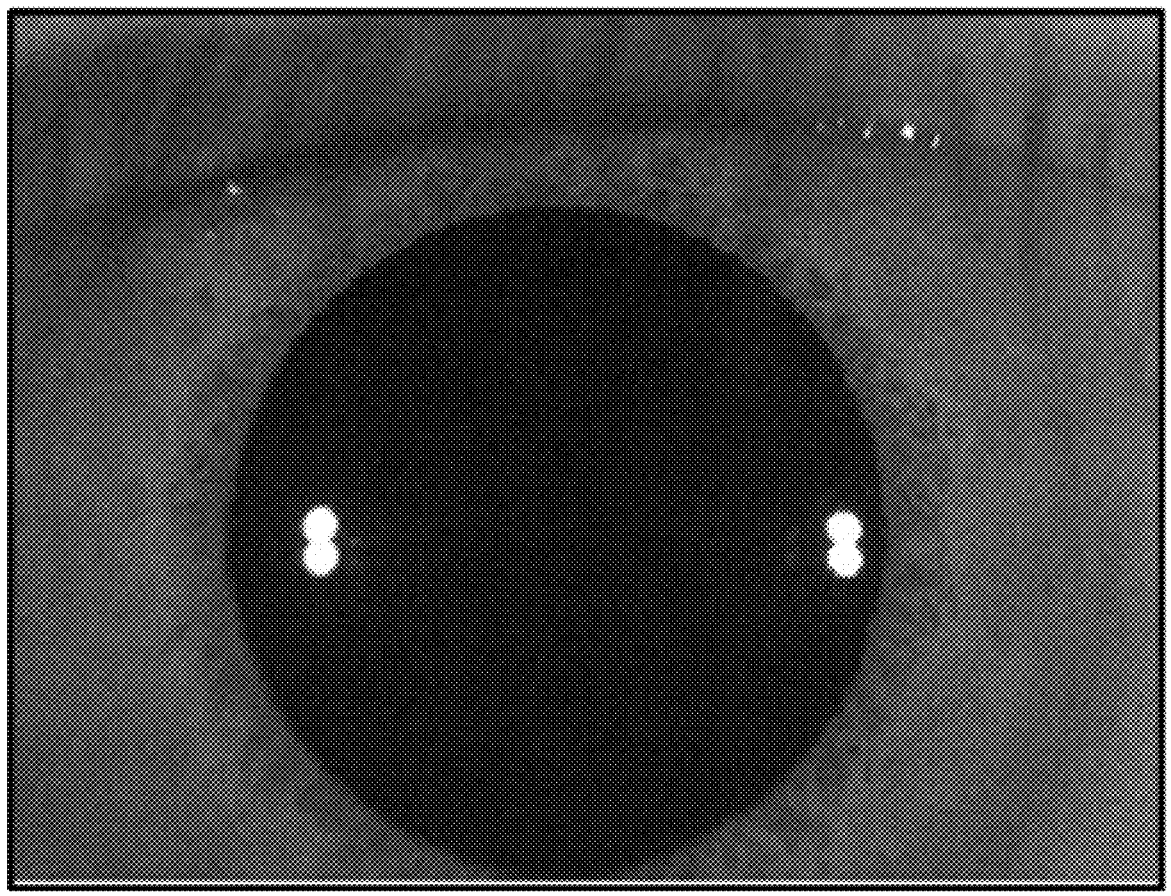
FIG. 2 is an illustration of a macro ocular image that may be produced by an embodiment.

The pupil monitor 120 produces macro ocular portraits such as exemplary macro ocular portrait 200 illustrated in FIG. 2. The macro ocular portrait 200 allows the operator of the ophthalmoscope 100 to monitor a subject's pupil position and condition. The operator may make a note of the pupil position, the focusing status, and other additional indicators of the state of the subject's pupil.

Hartmann Image

Figure 3:
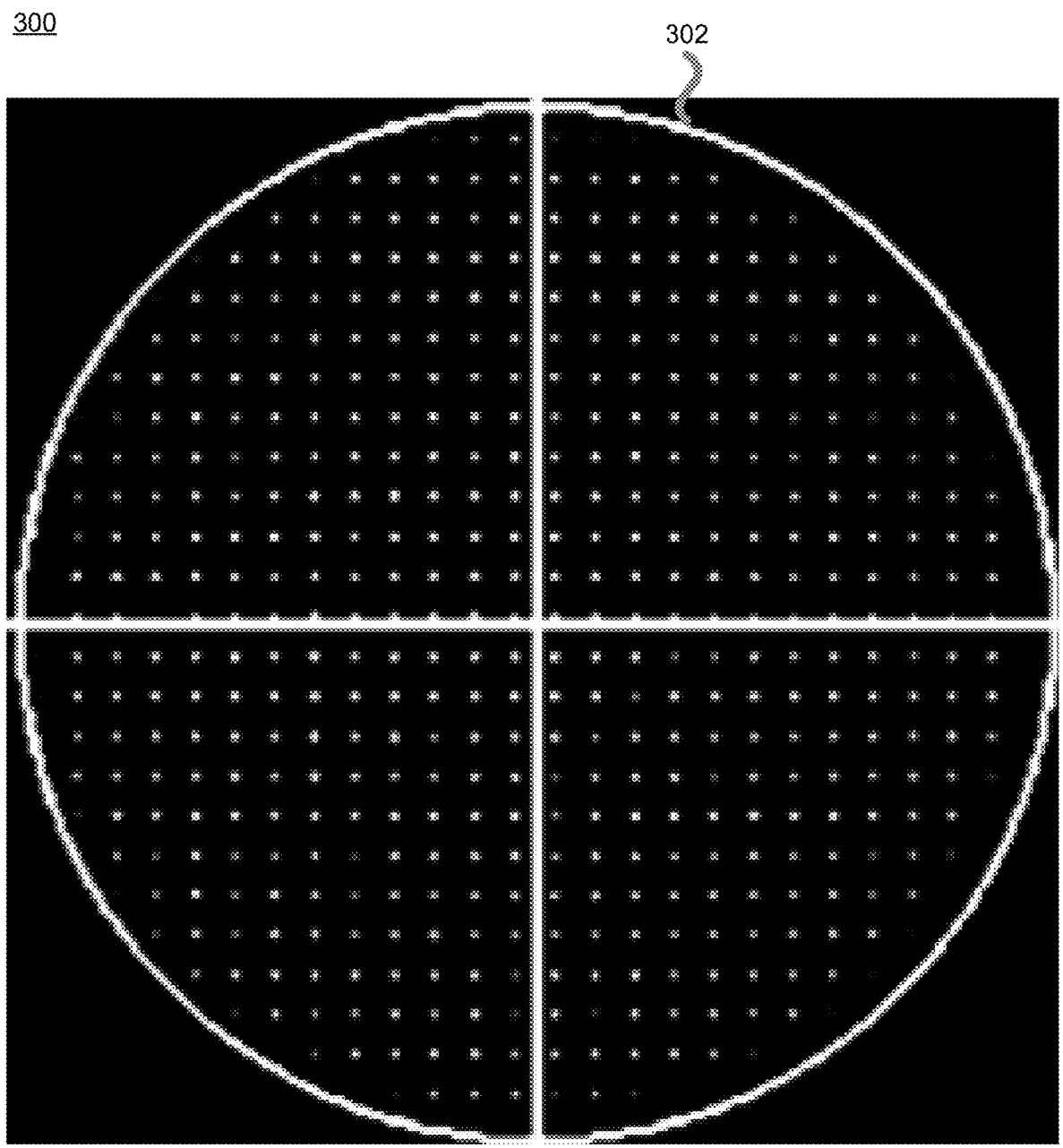
FIG. 3 is an illustration of a Shack-Hartmann image that may be produced by an embodiment.

It is also important to check the Shack-Hartmann image 300 as illustrated in FIG. 3 of the Shack-Hartmann sensor to make sure that sufficient spots are detected and inappropriate light doesn't come into the sensor so as to ensure accurate wavefront measuring. The Shack-Hartmann image 300 may be made up of a series of spots. If the wavefront is flat, then all the spots in the Shack-Hartmann image 300 line up on a grid. If the wavefront deviates from the flat state (e.g. aberrations) then the spots in the Shack-Hartmann image 300 will move away from the grid points. Spots may also change in size, shape, and intensity. Another type of Shack-Hartmann image 300 may use vectors instead of spots. The Shack-Hartmann image 300 may include a target 302. Portions of the Shack-Hartmann image 300 can disappear because of interference from the eye lid, eyelash, cataract, and other reasons. These factors which can lead to imaging failure should be resolved before imaging is performed.

The Shack-Hartmann image 300 is a tool for displaying wavefront information. More generally, the Shack-Hartmann image 300 may use a variety of methods of representing the wavefront information. Shack-Hartmann image 300 may include a plurality of markers. Wherein each marker may represent detected wavefront information in a particular area of the subject. Each marker among the plurality of markers may be displayed with a particular marker color. The particular marker color may be selected from a range of marker colors. The particular marker color for each particular marker may be selected based upon one or more of: a signal strength of the detected wavefront information in the particular area of the fundus; a magnitude of local aberration associated with the detected wavefront information in the particular area of the fundus; and a direction of local aberration associated with the detected wavefront information in the particular area of the fundus.

In one embodiment, each marker may be a spot. In which a diameter of each spot is correlated with the magnitude of the local aberration based upon the detected wavefront information.

In one embodiment, each marker is a vector. In which a length of each vector is correlated with the magnitude of the local aberration; and the direction of each vector is correlated with the direction of the local aberration.

It is difficult to monitor both images because these two images are displayed separately and they are not linked. Operators are forced to attempt to detect relationships between these two images. For example, even if some Shack-Hartmann spots disappear, the operator will have difficulty troubleshooting why this happened. Many kinds of factors can affect the Shack-Hartmann image such as pupil size, eye lid, eye lash, cataract, etc. It is difficult to assume which problem is affecting the Shack-Hartmann image.

Overlay Image

Figure 4:
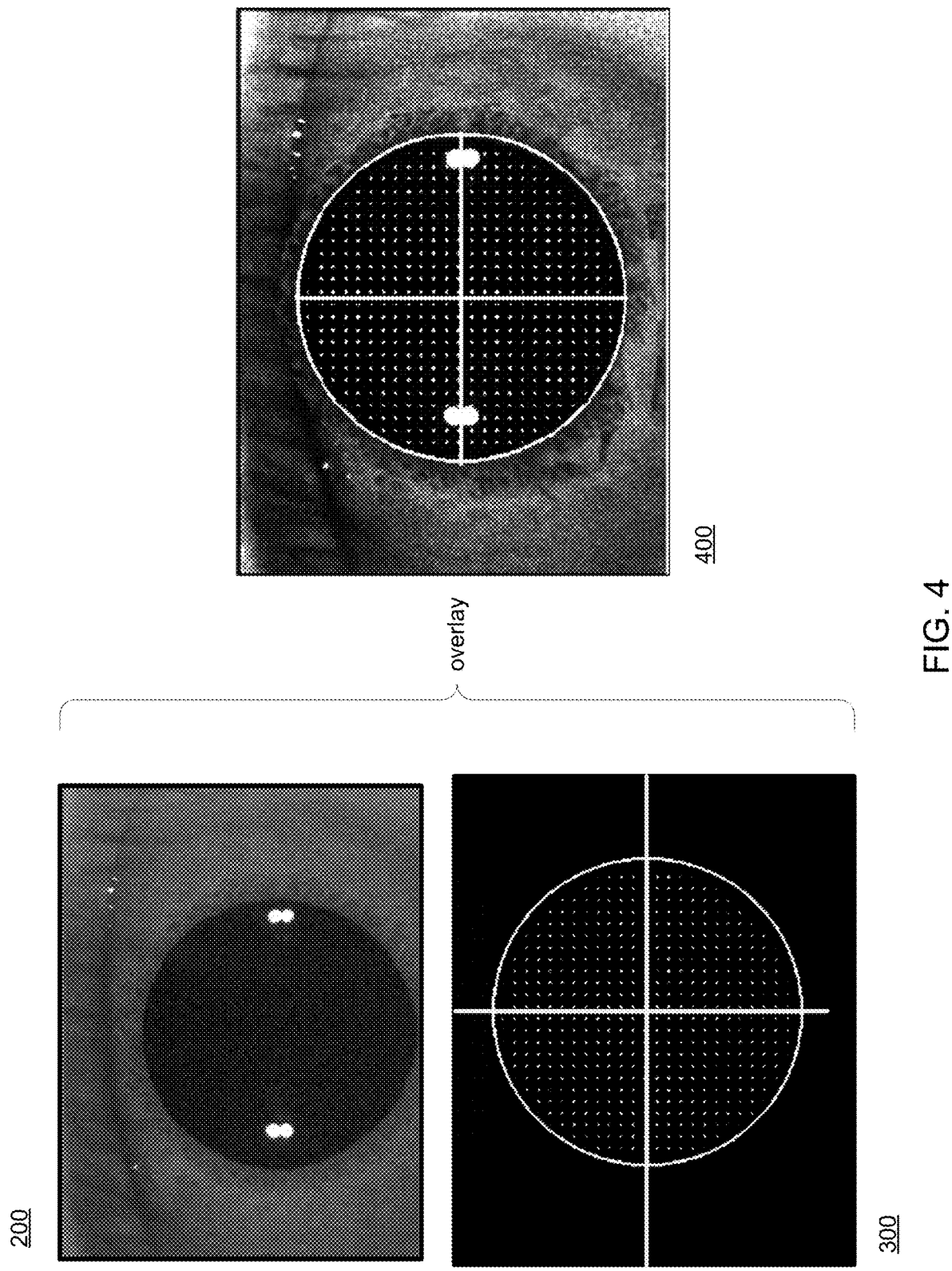
FIG. 4 is an illustration of an overlay image that may be produced by an embodiment.

The applicant has found a way to solve this problem, by having the AO-SLO control software display an overlay image 400 of the macro ocular portrait 200 and Shack-Hartmann image 300 as illustrated in FIG. 4. This innovation allows an operator to check the pupil status including position and condition and Shack-Hartmann image simultaneously so that you can realize what factor affect the Shack-Hartmann image 300. An operator can quickly see issues within a specific area of the Shack-Hartmann image 300 that are associated with a corresponding area of the macro ocular portrait 200. In an alternative embodiment, a series of overlay images 400 are produced and turned into an overlay video. The macro ocular portrait 200 may have a constant macro ocular refresh rate such as 30 Hz or 60 Hz to produce a macro ocular video. While a wavefront refresh rate of the wavefront information used to produce the may be Shack-Hartmann images 300 is highly variable. For example, the wavefront refresh rate may vary between 5-50 Hz. The refresh rate may vary depending on the signal strength of the wavefront information. In one embodiment, the overlay video refresh rate may be equal to refresh rate of the macro ocular video. In another embodiment, the overlay video refresh rate may be equal to which ever refresh rate is greater of the two refresh rates: the wavefront refresh rate and the macro ocular video refresh rate. In another embodiment, the overlay video refresh rate is a function of the wavefront refresh rate and the macro ocular video refresh rate.

Figure 5A:
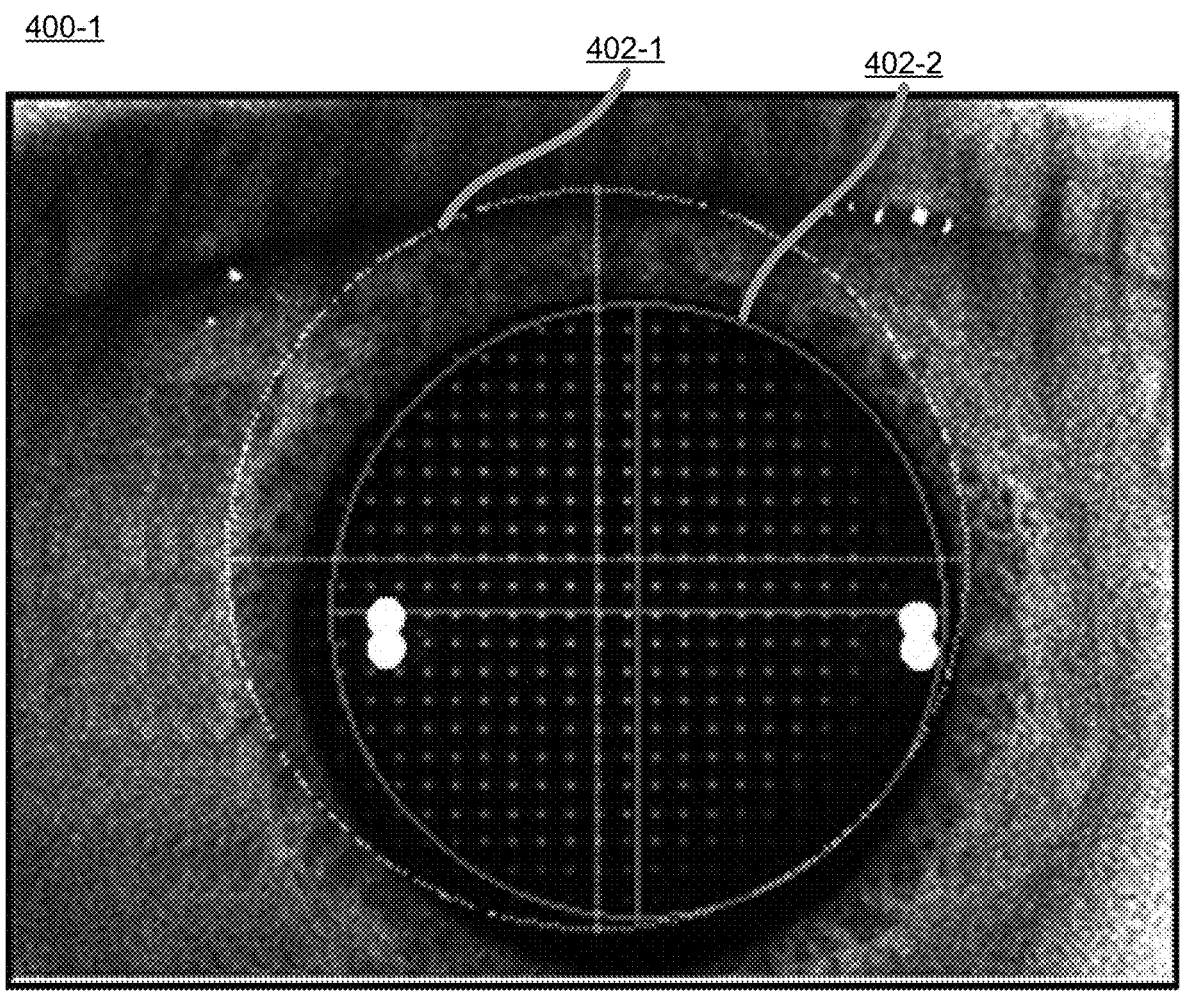
FIG. 5A-5E are illustrations of overlay images that may be produced by an embodiment.

Several different kinds of issues can appear in the overlay image 400. FIG. 5A is an illustration of an example of one of those issues in which the pupil has shifted relative to the measurement beam. In which case the AO-SLO software will display an overlay image 400 such as first exemplary overlay image 400-1. The pupil shifting can cause a lack of spots on Shack-Hartmann image 300. The first exemplary overlay image 400-1 illustrated in FIG. 5A also shows a first target 402-1 (white dashed line) and a second target 402-2 (gray solid line). The first target 402-1 (white dashed line) represents the optically appropriate position, size and position of the image Shack-Hartmann image 300, based on the center of the optical system and aperture size of the system. For example, a diameter of the first target 402-1 corresponds to the beam diameter of the incident light and/or wavefront measurement area. The size and position of the first target 402-1 relative to the macro ocular portrait 200 may be set during a calibration process. The ophthalmoscope 100 may include ability to adjust the size and position of the area that is being imaged. When the size and/or position of the imaging are then the size and/or position the first target may also change relative to the macro ocular portrait 200. While the second target 402-2 (gray solid line) represents the detected size and position of the pupil. The overlay image 400 may include at least one target.

The color of the second target 402-2 may change depending on the detected size of the pupil. The color of the second target 402-2 may also change depending on the artifacts detected in the macro ocular portrait. The color of the second target 402-2 may also change depending on artifacts detected in the wavefront information. These color changes may aid an operator in determining when the ophthalmoscope 100 is ready to obtain imaging data. The color of the first target 402-1 and/or the second target 402-2 may also change depending on the wavefront information. The first target 402-1 and/or the second target 402-2 may be displayed with a plurality of colors representing radial variation in the detected wavefront information.

Figure 5B:
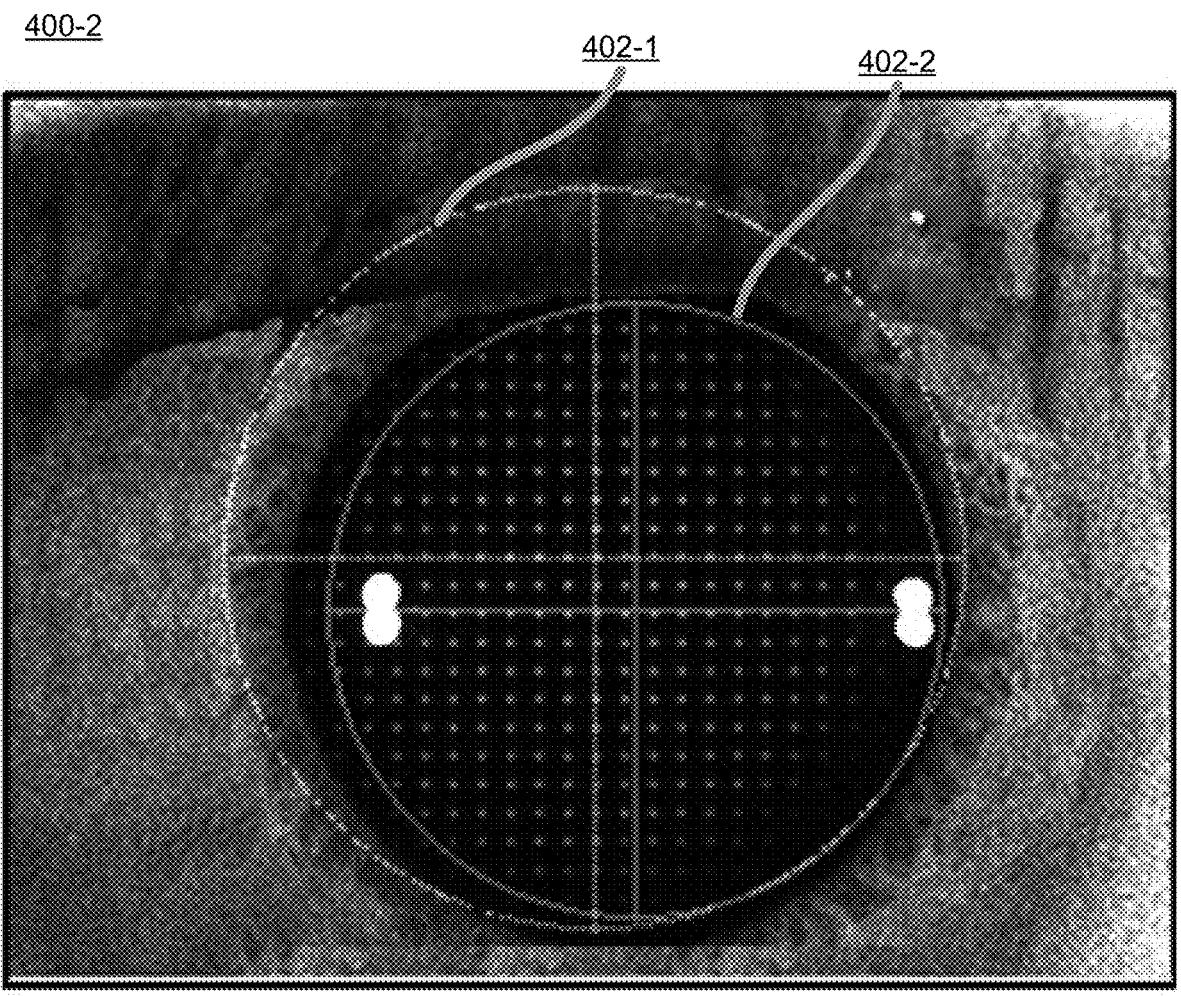

FIG. 5B is an illustration of a second exemplary overlay image 400-2 in which an eyelid is blocking a portion the illumination beam illustrated by target 402-1 (white dashed line). An operator can easily determine from this image 400-2 that the eyelid is blocking light resulting in a lack of spots within the pupil target 402-2 (gray solid line).

Figure 5C:
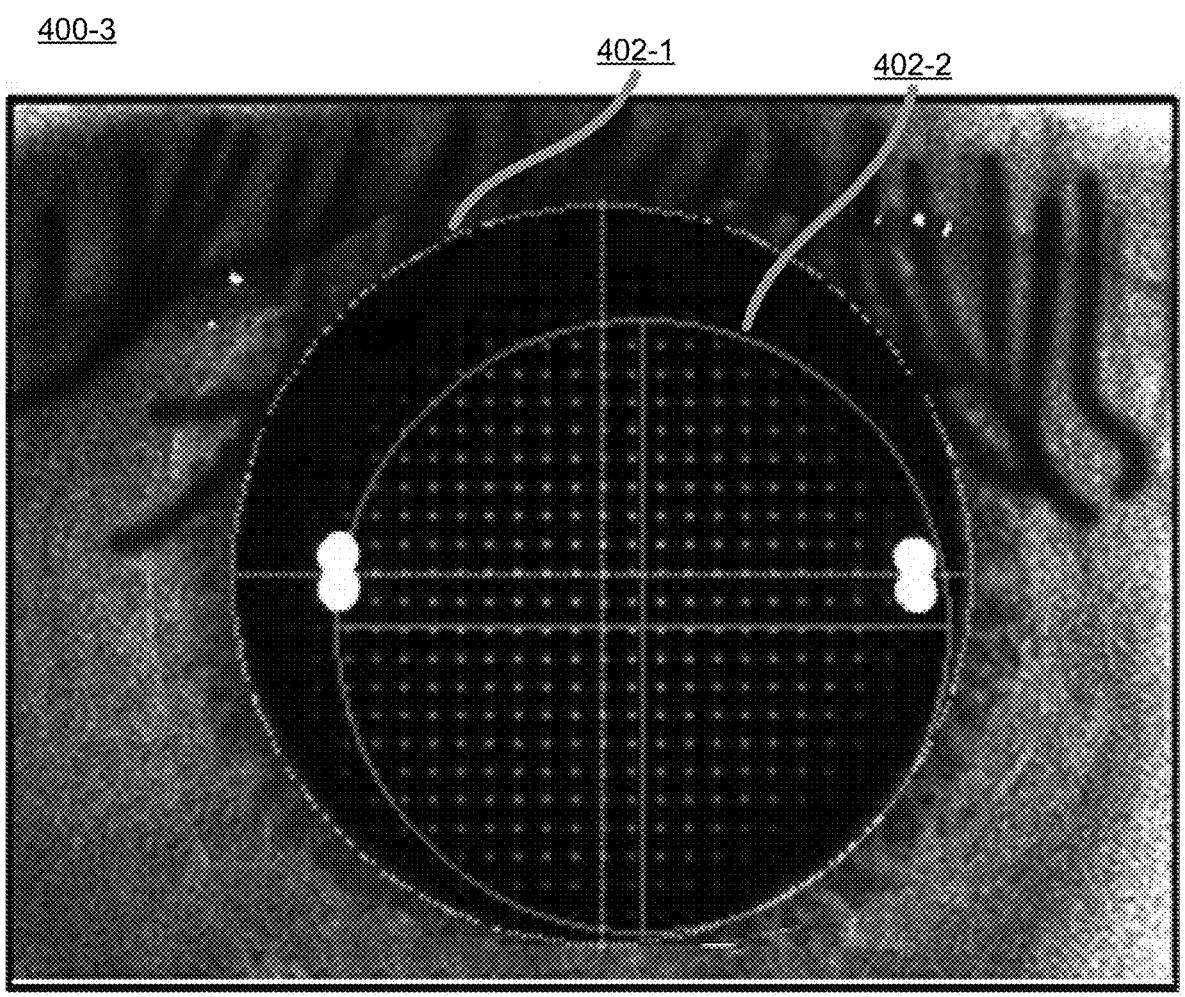

FIG. 5C is an illustration of a second exemplary overlay image 400-3 in which eyelashes are blocking a portion the illumination beam illustrated by target 402-1 (white dashed line). An operator can easily determine from this image 400-2 that the eyelashes are blocking light resulting in a lack of spots within the detected pupil target 402-2 (gray solid line).

The color of the target 402-1 may be used to communicate information to a user about the general status of the wavefront information. For example the color the first target may vary depending one or more of: a number of detected spots in the wavefront information; an average signal strength of the detected spots in the wavefront information, and presence of artifacts in the wavefront information. In which the spots are Shack-Hartmann spots.

Figure 5D:
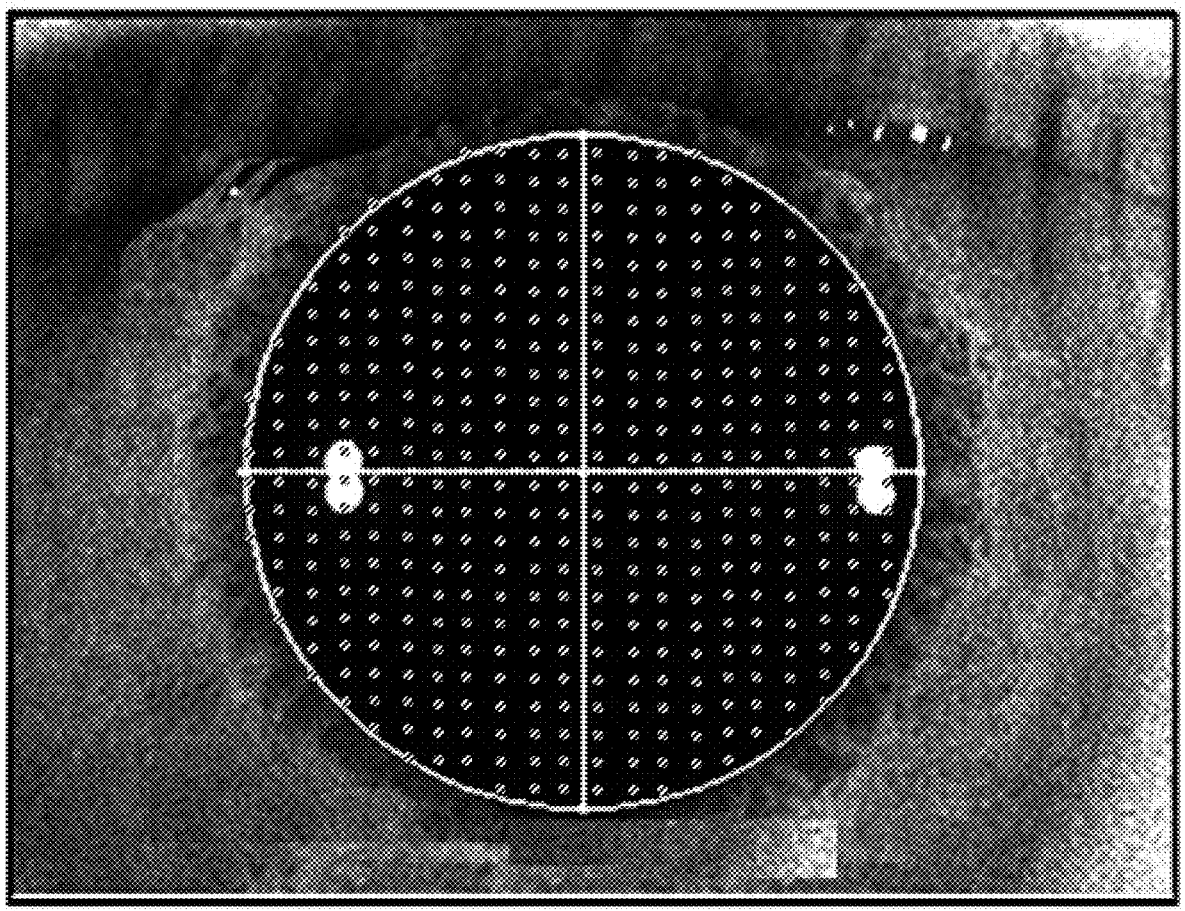

FIG. 5D is an illustration of a second exemplary overlay image 400-4 in which a different color is used for the Shack-Hartmann spots. Different colors may be used to display the Shack-Hartmann spots. This may be used to aid the operator from distinguishing the spots from the background. For example, the Shack-Hartmann spots may be green while the macro ocular portrait 200 is a gray scale image. The operator may be able to set the color of the Shack-Hartmann spots or it may be preset. The macro ocular portrait 200 may also be a color image, or a false color image.

Figure 5E:
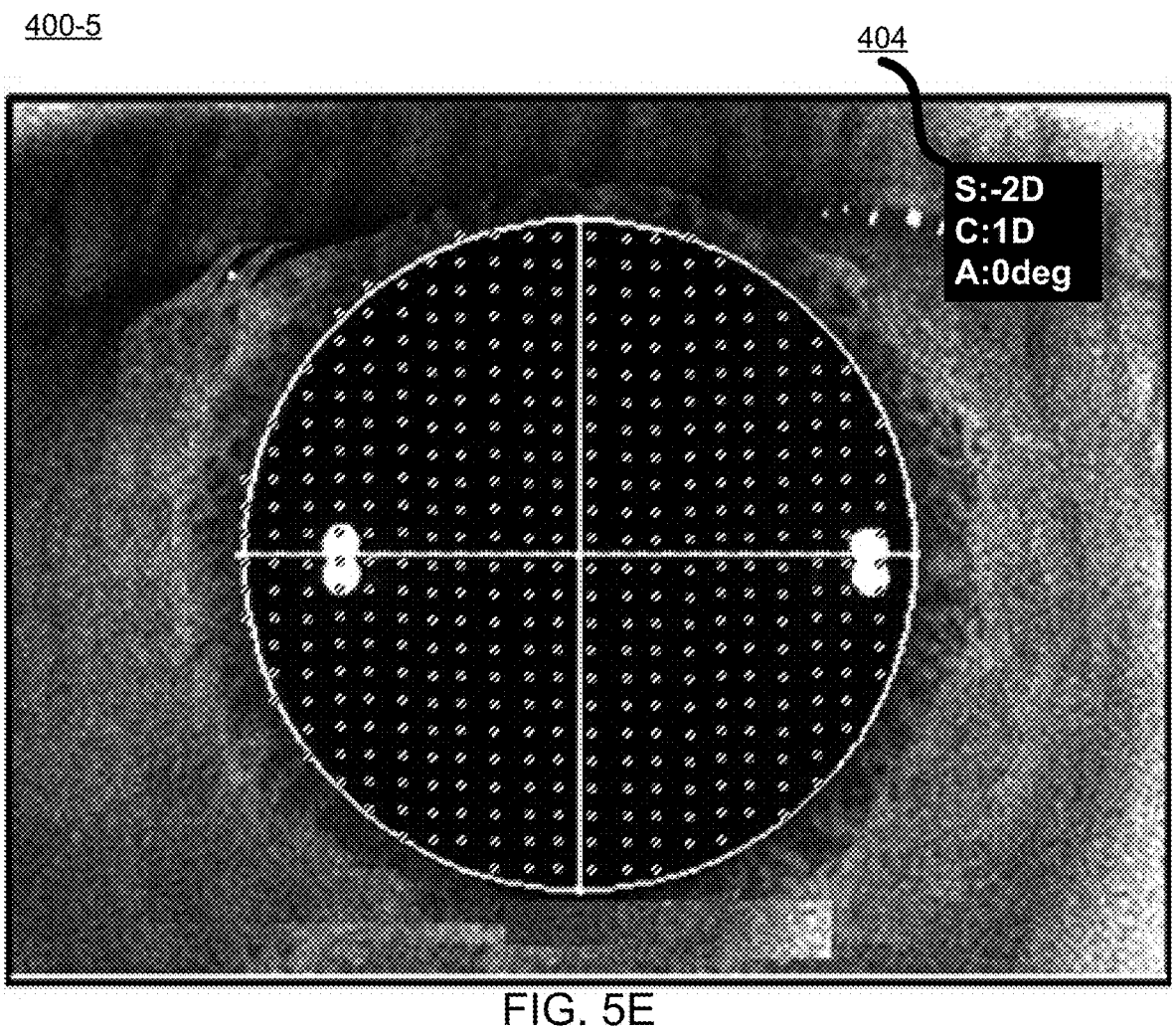

FIG. 5E is an illustration of a second exemplary overlay image 400-5 in which information 404 associated with the eye 111 is also displayed. The information 404 may be in color so as to be easily distinguishable against a highly variable background of the overlay image 400-5. The information 404 may include prescription information such as the spherical (S), cylinder (C), and axis (A). The prescription information may be entered or may be calculated based upon information from the wavefront sensor 115.

The macro ocular portrait 200 may include artifacts. An example, of artifacts may be the four white circles shown in FIG. 2. These artifacts may be reflections of the light source used for the pupil monitor 120. These artifacts may interfere with a user's ability to understand the wavefront information. In which case, these artifacts may be removed from overlay image 400.

Process

Figure 6:
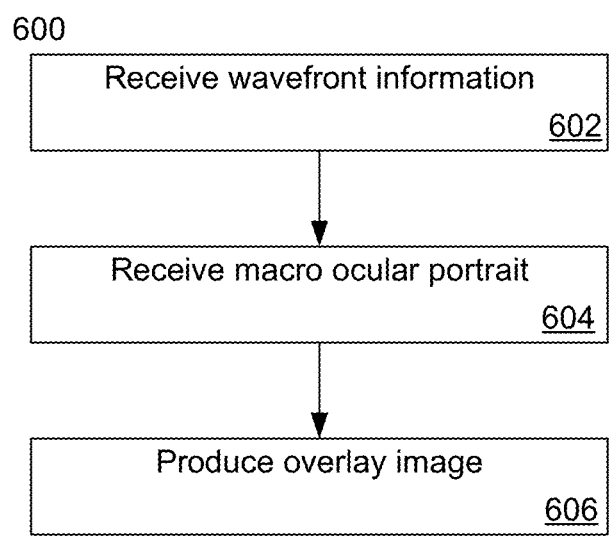
FIG. 6 is an illustration of a process that may be implemented in an embodiment.

FIG. 6 is an illustration of an image processing method 600 that may be used for processing images from an ophthalmic apparatus such as ophthalmoscope 100. A first step 602 may include receiving wavefront information such as Shack Hartmann image 300 from the ophthalmoscope 100. The wavefront information is representative of a wavefront of return light from a fundus of an eye. A second step 604 may include receiving a macro ocular portrait 200 of the eye 111. A third step 606 may include producing an overlay image 400 in which the wavefront information is overlaid on top of the macro ocular portrait 200.

Controller

Figure 7:
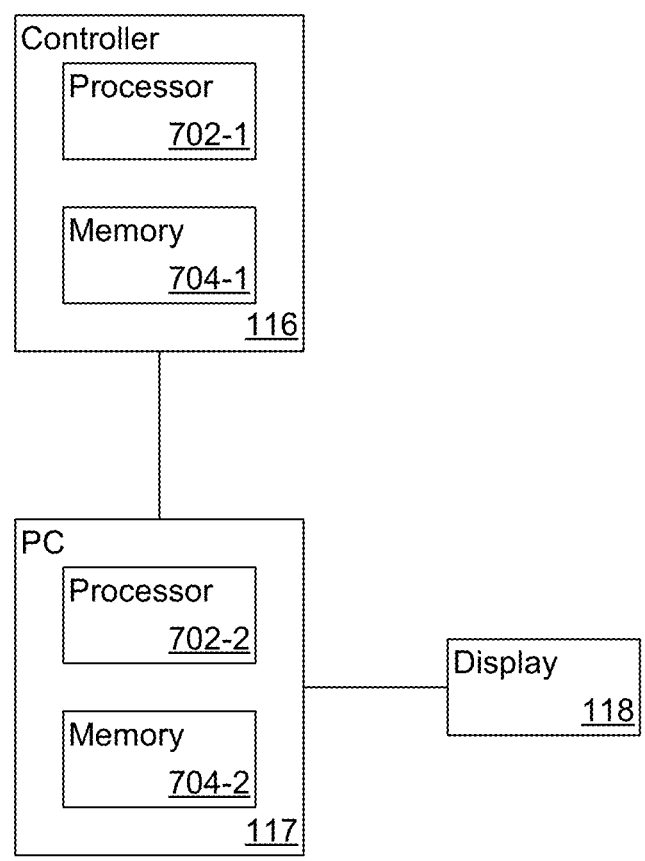
FIG. 7 is an illustration of a controller that may be used in an embodiment.

FIG. 7 is an illustration of the PC 116 and controller 117 that may be used in an embodiment. The controller 116 receives input signals and outputs control signals. The controller 116 may be a general purpose computer, a device specifically designed to controller the ophthalmoscope 100, or a hybrid device that uses some custom electronics along with a general purpose computer 117. The input signals and control signals maybe digital signals or analog signals. The controller 116 may include an analog to digital converter (ADC) and a digital to analog converter (DAC). The input signals may include one more signals such as a signal from the wavefront sensor 115, a signal from the detector 113, and one or more signals from one or more other sensors. The control signals may include a first control signal to a wavefront adjustment device 108 and signals to one or more of the scanners 109-1 and 109-2. The control signals may include additional signals to other components of the ophthalmoscope 100.

The controller 116 includes a processor 702-1. The processor 702-1 may be a microprocessor, a CPU, an ASIC, a DSP, and/or a FPGA. The processor 702-1 may refer to one or more processors that act together to obtain a desired result. The controller 116 may include a memory 704-1. The memory 704-1 may store calibration information. The memory 704-1 may also store software for controlling the ophthalmoscope 100. The memory 704 may be a form of a non-transitory computer readable storage medium. The non-transitory computer readable storage medium may include, for example, one or more of a hard disk, a random-access memory (RAM), a read only memory (ROM), a distributed storage system, an optical disk (CD, DVD or Blu-Ray Disc, a flash memory device, a memory card, or the like.

The controller 116 may be connected to a computer (PC) 117 via a direction connection, a bus, or via a network. The computer 117 may include input devices such as a keyboard, a mouse or a touch screen. The controller may include input device such as a keyboard, a mouse or a touch screen, knobs, switches, and/or buttons. The computer 117 may be connected to a display 118. The results of the ophthalmoscope 100 may be presented to a user via the display 118. The production of the phase maps which are used to control the wavefront adjustment device 108 may be created by the controller 116 independently of the PC 117 or with the help of the PC 117. The PC may include a processor 702-2 and a memory 704-2.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. An ophthalmic apparatus that irradiates an eye of a subject with measuring light and gathers return light of the measuring light from a fundus of the eye comprising:
    a processor;
    a memory;
    a Shack-Hartmann sensor that detects a Shack-Hartmann image of the return light in real time; and
    a pupil monitor that outputs to the memory a macro ocular portrait of the eye in real time;
    wherein the processor produces an overlay image in which the real-time Shack-Hartmann image and a first target image are overlaid on the real-time macro ocular portrait, and displays the overlay image on a display device as a moving image, and
    the first target image represents a position and a size of the real-time Shack-Hartmann image detected by the Shack-Hartmann sensor, and a position of the first target image on the real-time macro ocular portrait is shifted by moving an irradiation position of the measuring light relative to the eye.

2. The ophthalmic apparatus according to claim 1, wherein: the real-time Shack-Hartmann image is represented in the overlay image in a different color from the color used in the real-time macro ocular portrait in the overlay image.

3. The ophthalmic apparatus according to claim 1, further comprising the display device which displays the overlay image.

4. The ophthalmic apparatus according to claim 1, wherein the first target image is set during a calibration process.

5. The ophthalmic apparatus according to claim 4, wherein a relative position of the first target image moves relative to the real-time macro ocular portrait if the position of the eye that is irradiated by the ophthalmic apparatus moves.

6. The ophthalmic apparatus according to claim 4, wherein a diameter of the first target image changes relative to the real-time macro ocular portrait if a pupil of the eye that is irradiated by the ophthalmic apparatus changes in size.

7. The ophthalmic apparatus according to claim 6, wherein a second target color of the first target image is changed based upon one or more of:
    a diameter of the detected area of the pupil; and
    presence of artifacts in the real-time macro ocular portrait.

8. The ophthalmic apparatus according to claim 1, the overlay image further comprises: aberration information of the eye that is calculated on the basis of the Shack-Hartmann image.

9. The ophthalmic apparatus according to claim 1, wherein: the overlay image is displayed on the display device in response to receiving a display mode setting to display the overlay image.

10. The ophthalmic apparatus according to claim 1, wherein
    the Shack-Hartmann sensor outputs the real-time Shack-Hartmann image in a first refresh rate;
    the pupil monitor outputs the real-time macro ocular portrait of the eye in a second refresh rate;
    the first refresh rate of the real-time Shack-Hartmann image is different from the second refresh rate; and
    a third refresh rate of the overlay image is the greater of the first refresh rate and the second refresh rate.

11. The ophthalmic apparatus according to claim 1, wherein the processor removes artifacts from the overlay image, wherein the artifacts come from the real-time macro ocular portrait.

12. The ophthalmic apparatus according to claim 1, wherein:
    the Shack-Hartmann image is represented by a plurality of markers;
    each marker among the plurality of markers is representative of detected Shack-Hartmann image in a particular area of the fundus;
    each marker among the plurality of markers is displayed with a particular marker color;
    the particular marker color is selected from a range of marker colors; and
    the particular marker color for each particular marker is selected based upon one or more of:
        a signal strength of the detected Shack-Hartmann image in the particular area of the fundus;
        a magnitude of local aberration associated with the detected Shack-Hartmann image in the particular area of the fundus; and
        a direction of local aberration associated with the detected Shack-Hartmann image in the particular area of the fundus.

13. The ophthalmic apparatus according to claim 12, wherein: each marker is a spot, a diameter of each spot is correlated with the magnitude of the local aberration.

14. The ophthalmic apparatus according to claim 12, wherein:
    each marker is a vector,
    a length of each vector is correlated with the magnitude of the local aberration; and
    the direction of each vector is correlated with the direction of the local aberration.

15. The ophthalmic apparatus according to claim 1, wherein the processor further overlays a second target image on the overlay image, and the second target image represents a detected size and position of a pupil of the eye.

16. The ophthalmic apparatus according to claim 1, wherein a first target color of the first target image is changed based on one or more of:
    a number of detected spots in the real-time Shack-Hartmann image;
    an average signal strength of the detected spots in the real-time Shack-Hartmann image; and
    presence of artifacts in the real-time Shack-Hartmann image.

17. An ophthalmic apparatus that irradiates an eye of a subject and gathers return light from a fundus of the eye, comprising:

a processor;
a memory;
a Shack-Hartmann sensor that outputs to the memory a Shack-Hartmann image; and
a pupil monitor that outputs to the memory a macro ocular portrait of the eye,
wherein the processor produces an overlay image in which the Shack-Hartmann image is overlaid on top of the macro ocular portrait, and a first target which is overlaid over the macro ocular portrait,
wherein the first target is representative of an area of the eye that is irradiated by the ophthalmic apparatus, and
wherein a first target color of the first target image is changed based on one or more of:
a number of detected spots in the Shack-Hartmann image;
an average signal strength of the detected spots in the Shack-Hartmann image; and
presence of artifacts in the Shack-Hartmann image.

18. An ophthalmic image processing method for images from an ophthalmic apparatus comprising:

irradiating an eye of a subject with measuring light;
receiving, in real time, Shack-Hartmann image that is representative of a wavefront of return light of the measuring light from a fundus of the eye;
receiving, in real time, a macro ocular portrait of the eye;
producing, in real time, an overlay image in which the real-time Shack-Hartmann image and a first target image are overlaid on the real-time macro ocular portrait, and
displaying the overlay image on a display device as a moving image,
wherein the first target image represents a position and a size of the real-time Shack-Hartmann image, and a position of the first target image on the real-time macro ocular portrait is shifted by moving an irradiation position of the measuring light relative to the eye.

19. A non-transitory computer readable medium encoded with instructions for a computer to perform a method for processing images from an ophthalmic apparatus comprising:

irradiating an eye of a subject with measuring light;
receiving, in real time, a Shack-Hartmann image that is representative of a wavefront of return light of the measuring light from a fundus of the eye;
receiving, in real time, a macro ocular portrait of the eye;
producing, in real time, an overlay image in which the real-time Shack-Hartmann image and a first target image are overlaid on the real-time macro ocular portrait as a moving image, and
displaying the overlay image on a display device,
wherein the first target image represents a position and a size of the real-time Shack-Hartmann image, and a position of the target image on the real-time macro ocular portrait is shifted by moving an irradiation position of the measuring light relative to the eye.

* * * * *